United States Patent
Liao et al.

(10) Patent No.: US 9,103,778 B2
(45) Date of Patent: Aug. 11, 2015

(54) IMAGE-BASED REFRACTIVE INDEX MEASURING SYSTEM

(71) Applicant: NATIONAL APPLIED RESEARCH LABORATORIES, Taipei (TW)

(72) Inventors: Tai-Shan Liao, Hsinchu (TW); Chi-Hung Huang, Hsinchu (TW); Chih-Chieh Wu, HsinChu (TW); Din Ping Tsai, Hsinchu (TW); Shih-Jie Chou, Hsinchu (TW); Cheng-Fang Ho, Hsinchu (TW)

(73) Assignee: National Applied Research Laboratories, Taipei (TW)

( * ) Notice: Subject to any disclaimer, the term of this patent is extended or adjusted under 35 U.S.C. 154(b) by 312 days.

(21) Appl. No.: 13/836,991

(22) Filed: Mar. 15, 2013

(65) Prior Publication Data
US 2014/0192183 A1   Jul. 10, 2014

(30) Foreign Application Priority Data
Jan. 10, 2013   (TW) .............................. 102100988 A

(51) Int. Cl.
*G01N 21/41* (2006.01)
*G06K 9/00* (2006.01)
*G01N 21/43* (2006.01)

(52) U.S. Cl.
CPC ..................................... *G01N 21/43* (2013.01)

(58) Field of Classification Search
CPC ................................................... A61B 1/00009
USPC ........................................... 348/135; 356/135
See application file for complete search history.

(56) References Cited

U.S. PATENT DOCUMENTS

| | | | | |
|---|---|---|---|---|
| 5,005,972 | A   * | 4/1991  | Goldberg ....................... | 356/135 |
| 8,073,324 | B2 * | 12/2011 | Tsai .............................. | 396/544 |
| 8,239,144 | B2 * | 8/2012  | Fedele ........................... | 702/35 |
| 2007/0076950 | A1 * | 4/2007 | Shah ............................. | 382/170 |
| 2007/0098290 | A1 * | 5/2007 | Wells ............................ | 382/254 |
| 2009/0046277 | A1 * | 2/2009 | Amamiya et al. ............ | 356/135 |

(Continued)

FOREIGN PATENT DOCUMENTS

| | | |
|---|---|---|
| TW | D111526 | 6/2006 |
| TW | D127363 | 2/2009 |

(Continued)

OTHER PUBLICATIONS

Dictionary.com Diopter Mar. 12, 2015 http://dictionary.reference.com/browse/diopter?s=t.*

*Primary Examiner* — Dave Czekaj
*Assistant Examiner* — Alison Slater
(74) *Attorney, Agent, or Firm* — Wang Law Firm, Inc.; Li K. Wang; Stephen Hsu

(57) ABSTRACT

An image-based refractive index measuring system comprises an optical device and an electronic device. The optical device is used to guiding an external light which is passed through an analyte. The electronic device comprises an image capture module, an image analyze module and a display module. The image capture module generates a first image by capturing the external light source. The image analyze module connects to the image capture module to receive the first image, and analyzes the first image in order to generate an analytical result comprising the refractive index of the analyte. The display module connects to the image analyze module to receive and display the analytical result.

8 Claims, 4 Drawing Sheets

(56) References Cited

U.S. PATENT DOCUMENTS

2009/0091799 A1* 4/2009 Tabata et al. ................. 358/3.28
2010/0080991 A1* 4/2010 Kishioka et al. .......... 428/355 R
2011/0135170 A1* 6/2011 Wang ............................ 382/128
2011/0264006 A1* 10/2011 Ali et al. ........................ 600/587
2012/0057776 A1* 3/2012 Tao et al. ....................... 382/154

FOREIGN PATENT DOCUMENTS

TW M395161 12/2010
TW M398117 2/2011

\* cited by examiner

US 9,103,778 B2

IMAGE-BASED REFRACTIVE INDEX MEASURING SYSTEM

CROSS-REFERENCE TO RELATED APPLICATION

This application claims the benefit of Taiwan Patent Application No. 102100988, filed on Jan. 10, 2013, in the Taiwan Intellectual Property Office, the disclosure of which is incorporated herein in its entirety by reference.

BACKGROUND OF THE INVENTION

1. Field of the Invention

The present invention relates to a measuring system, in particular to an image-based refractive index measuring system.

2. Description of the Related Art

Currently, the applications of the refractive index are relatively extensive, for example, a sugar meter that measures the juice sweetness or measures the water salinity that both may use the principle of refraction. The conventional sugar refractive index meter or the refractometer in circulation such as the refractometers disclosed by Republic of China Patent D111526 or D127363. The refractometer is basically a round pipe body that a duckbill shaped portion of the front end is a measure end, which having a head shaped lift cover and having a rectangular lens therein, the round pipe body may drop the liquid into the lens, and the intermediate round pipe body is a gripping portion, the terminal end is a drum-shaped eyecup end, which may view the scale on the lens to know the predicting refractive index or the concentration. In the conventional technology, the user has to visually interpret the scale on the lens by the eye, so as to know the predicting refractive index and the concentration of the predicting analyte. In the long-term use of the environment, it is easy to cause the occupational injury for the user's eyes.

In addition, the sugar detection meter in the Republic of China Patent M398117 and the juice sweetness detection device in the Republic of China Patent M395161, are arranged for measuring the refractive index by the optical manner. However, the sugar detection meter uses the grating spectrometer parts and the infrared detection element architecture, which lead to the complexity of the system design and costly. Therefore, it is more complex in manipulation and the higher cost is the biggest deficiency while using such type of meter.

SUMMARY OF THE INVENTION

In view of the drawbacks of the prior art, one object of the present invention is to provide an image-based refractive index measuring system comprising at least an optical device and an electronic device. The optical device may guide an external light passed through an analyte. The electronic device comprises an image capture module, an image analyze module and a display module. The image capture module may generate a first image by capturing the external light source. The image analyze module is connected to the image capture module, and may receive the first image and analyze the first image in order to generate an analytical result comprising a refractive index of the analyte. The display module is connected to the image analyze module, and may receive and display the analytical result. Wherein, the optical device is detachably engaged to the electronic device, so as to guide the external light into the image capture module.

Preferably, the image analyze module may include a pixel conversion unit, a contrast line space coordinate detection unit, a contrast line space-parameter space coordinate conversion unit, a full-pixel parameter space coordinate comparison unit, a contrast line slant angle determining unit, and a refractive index control unit. The pixel conversion unit may convert the first image in order to obtain a second image via a pixel conversion formula. The contrast line space coordinate detection unit is connected to the pixel conversion unit, and may analyze the second image in order to obtain a gradient value G of each pixel point (x,y) in the second image, and may determine at least one the pixel point (x,y) to be a contrast line characteristic point when the gradient value G of the pixel point (x,y) is greater than a threshold value K, and calculate an average value of each coordinate of all the contrast line characteristic points in the second image to obtain a contrast line of the second image and a contrast line space coordinate thereof. The contrast line space-parameter space coordinate conversion unit is connected to the contrast line space coordinate detection unit, and may convert all the contrast line characteristic points into a plurality of parameter space coordinate mapping curves according to a coordinate converting formula. The full-pixel parameter space coordinate comparison unit is connected to the contrast line space-parameter space coordinate conversion unit, and may accumulate the parameter space coordinate mapping curves by an accumulator in order to obtain a maximum parameter space coordinate of the parameter space coordinate mapping curves in a polar coordinate, so as to obtain a slant angle of the contrast line. The contrast line slant angle determining unit is connected to the full-pixel parameter space coordinate unit, and may determine whether the slant angle is smaller than a default value predetermined by the contrast line slant angle determining unit. When the slant angle is smaller than the default value, the refractive index of the analyze is obtained by a refractive index control unit according to a correspondence base of contrast line space coordinate and the refractive index, and when the slant angle is greater than the default value, the display module generates a reminding signal.

Preferably, a color signal of the first image may be converted to a grayscale signal by the pixel conversion formula in order to obtain the second image, the pixel conversion formula is in compliance with following equation: gr=0.299*Ri+0.587*Gi+0.114*Bi; wherein, Ri, Gi and Bi are color gradation values of red, green and blue respectively in the first image, gr is a grayscale value in the second image, the grayscale value may range from 0 to 255.

Preferably, a convolution calculation is conducted to each pixel point (x,y) in the second image with a horizontal Sobel operation mask (Mask_i) and a vertical Sobel operation mask (Mask_j), respectively, by the contrast line space coordinate detection unit in order to obtain a horizontal gradient strength (Gi) and a vertical gradient strength (Gj) of each pixel) point (x,y), the gradient value satisfies $G=\sqrt{(G_i)^2+(G_j)^2}$.

Preferably, the coordinate conversion formula is in compliance with the following equation: $r=x\cos\theta+y\sin\theta$; wherein, r is a distance between any pixel point (x,y) and pole of the polar coordinate, θ is an angle between a polar axis and the line segment of the pixel point (x, y) and the pole of the polar coordinate.

Preferably, the optical device comprises a prism base, a transparent window, a prism capable of producing a full reflection, an adapter lens, a coupling element, and a lens barrel. The prism base includes an accommodating space therein. The transparent window may be obliquely laminated on one side of the prism base. The prism may be disposed in the accommodating space of the prism base and laminated obliquely on the transparent window. A side of the adapter lens may face to a terminal face of the prism. The coupling element may be disposed as facing the adapter lens near an opposite side of the terminal face of the prism. The lens barrel is a hollow structure, and may female joint the prism base to substantially accommodate the prism, the adapter lens and the coupling element. Wherein, the optical device is detachably engaged to the electronic device may through the coupling element.

Preferably, the coupling element may be a magnetic component.

Preferably, the electronic device may further comprise a sound reminding module that issues a high-frequency sound signal and a low-frequency sound signal respectively according to the comparison between a reference value and the refractive index.

Preferably, the sound reminding module issues the high-frequency sound signal when the refractive index is higher than a reference value or the sound reminding module issues the low-frequency sound signal when the refractive index is not higher than the reference value.

The image-based refractive index measuring system according to the present invention may have the following advantages:

According to the image-based refractive index measuring system of the present invention, the optical device only needs to be simply disposed in the electronic device that having an image capturing function, and the refractive index of the analyte would be quickly and accurately obtained by the image processing manner, which not only reduces the manufacturing costs, but also does not require complex steps, and greatly enhances the simplicity of use for the user.

DETAILED DESCRIPTION OF THE PREFERRED EMBODIMENTS

Figure 1:
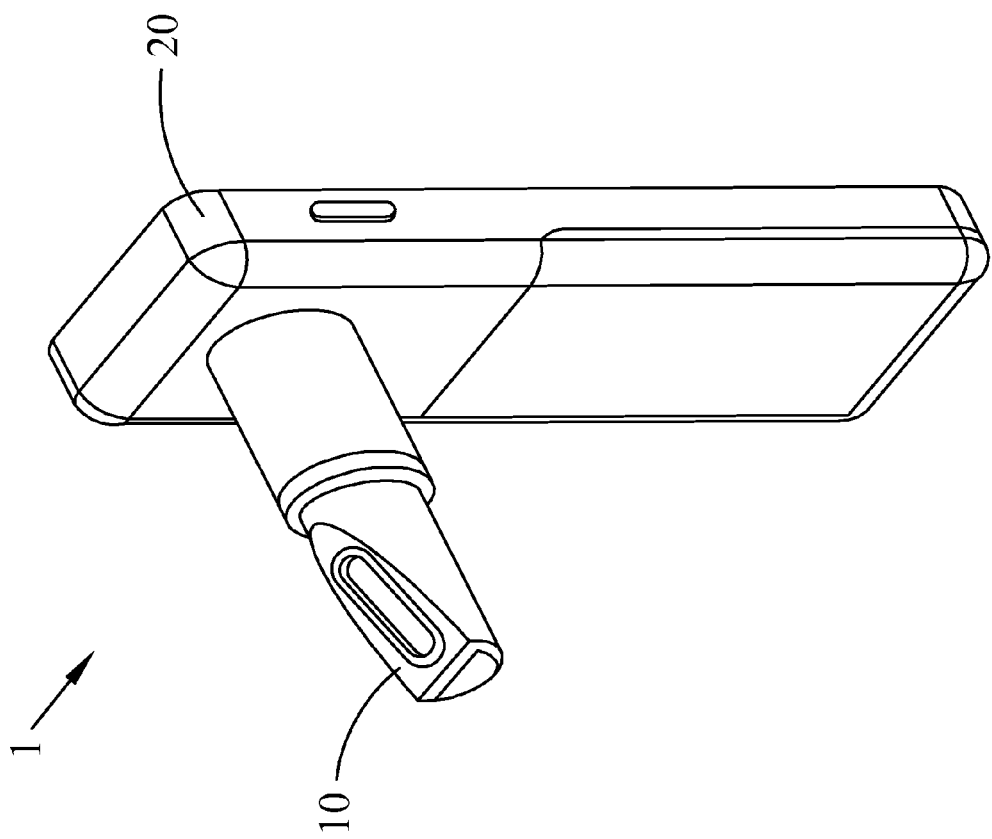
FIG. 1 is a first schematic diagram of the image-based refractive index measuring system according to the present invention.
Figure 2:
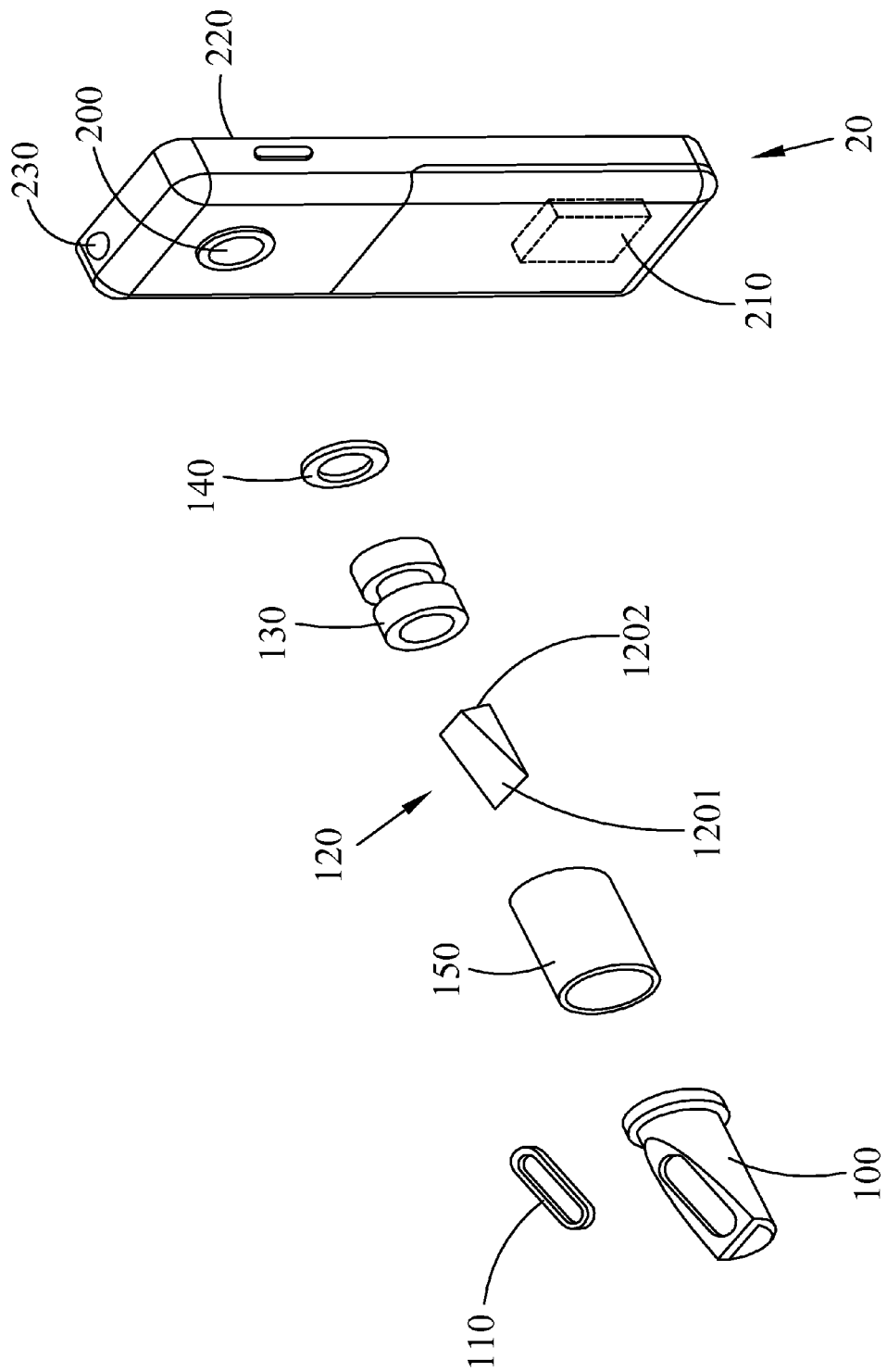
FIG. 2 is a second schematic diagram of the image-based refractive index measuring system according to the present invention.

With reference to FIG. 1 and FIG. 2, in which FIG. 1 is a first schematic diagram of the image-based refractive index measuring system and FIG. 2 is a second schematic diagram of the image-based refractive index measuring system according to the present invention. As show in FIG. 1, the image-based refractive index measuring system 1 of the present invention includes an optical device 10 and an electronic device 20. As show in FIG. 2, the electronic device 20 includes an image capture module 200, an image analyze module 210, and a display module 220. The optical device 10 includes a prism base 100, a transparent window 110, a prism 120 capable of producing total internal reflection, an adapter lens 130, a coupling element 140, and a lens barrel 150. Wherein, with the prism base 100 having an accommodating space therein, the transparent window 110 may be obliquely laminated on one side of the prism base 100, the prism 120 may be disposed in the accommodating space of the prism base 100 and laminated obliquely on the transparent window 110, a side of the adapter lens 130 may face to a terminal face 1202 of the prism 120, the coupling element 140 may be disposed to face the adapter lens 130 near an opposite side of the terminal face 1202 of the prism 120. The lens barrel 150 may be a hollow structure, and may joint to the prism base 100 to substantially accommodate the prism 120, the adapter lens 130 and the coupling element 140. In addition, the optical device 10 is detachably engaged to the electronic device 20 may through the coupling element 140, the coupling element 140 may be a magnetic component.

It is worth noting that the electronic device 20 may further include a sound reminding module 230 that issues a high-frequency sound signal and a low-frequency sound signal respectively according to the comparison between a reference value and the refractive index. Wherein, the sound reminding module 230 issues the high-frequency sound signal when the refractive index is higher than a reference value or the sound reminding module 230 issues the low-frequency sound signal when the refractive index is not higher than the reference value.

Figure 3:
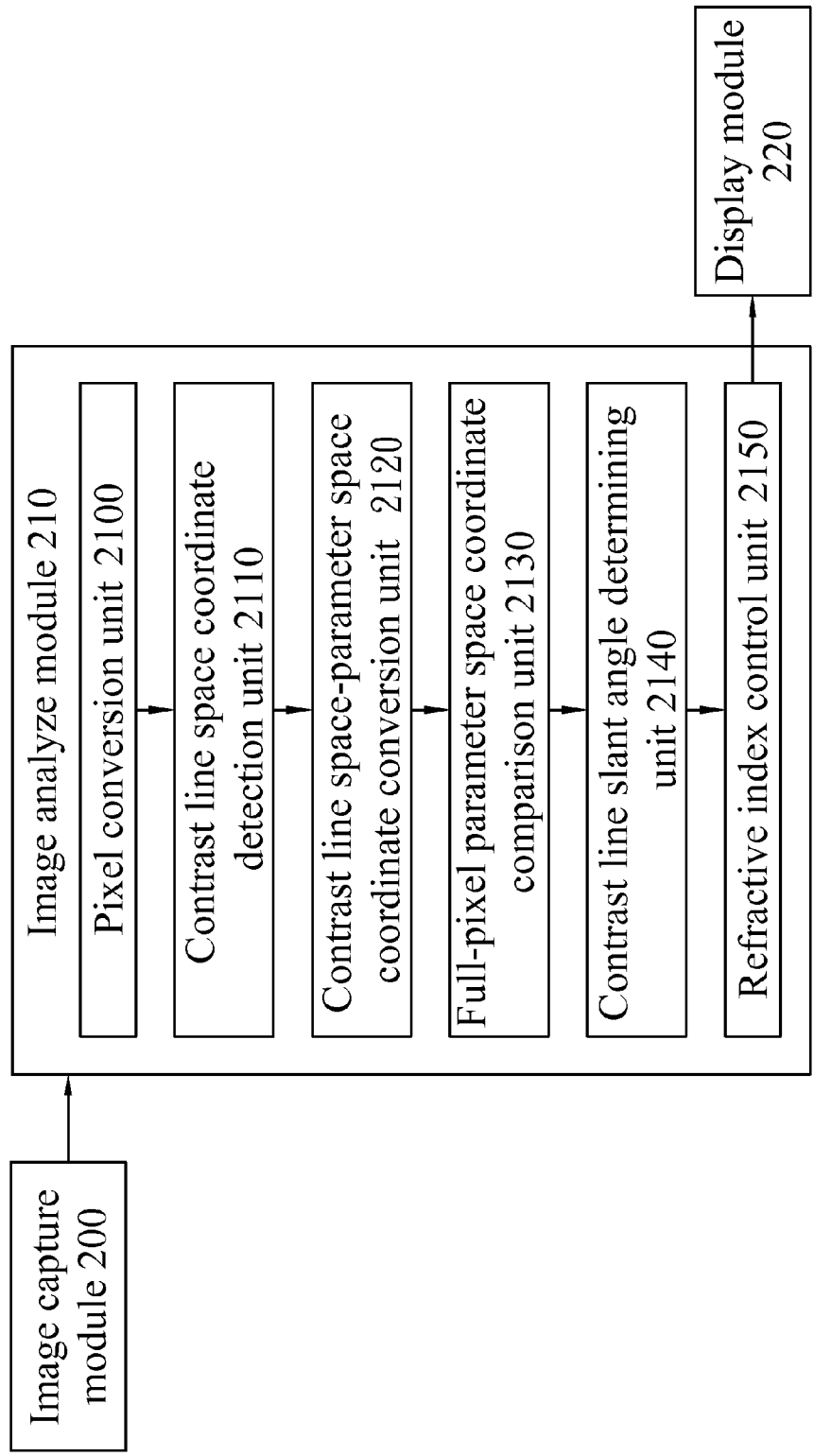
FIG. 3 is a third schematic diagram of the image-based refractive index measuring system according to the present invention.

With reference to FIG. 3, in which a third schematic diagram of the image-based refractive index measuring system according to the present invention is depicted. As show in FIG. 3, the image analyze module 210 may include a pixel conversion unit 2100, a contrast line space coordinate detection unit 2110, a contrast line space-parameter space coordinate conversion unit 2120, a full-pixel parameter space coordinate comparison unit 2130, a contrast line slant angle determining unit 2140, and a refractive index control unit 2150. The pixel conversion unit 2100 may convert the first image in order to obtain a second image via a pixel conversion formula. The contrast line space coordinate detection unit 2110 is connected to the pixel conversion unit 2100, and may analyze the second image in order to obtain a gradient value G of each pixel point (x,y) in the second image, and may determine the pixel point (x,y) to be a contrast line characteristic point when the gradient value G is greater than a threshold value K, and calculate an average value of a coordinate of all the contrast line characteristic points in the second image to obtain a contrast line of the second image and a contrast line space coordinate thereof. The contrast line space-parameter space coordinate conversion unit 2120 is connected to the contrast line space coordinate detection unit 2110, and may convert all the contrast line characteristic points into a plurality of parameter space coordinate mapping curves according to a coordinate converting formula. The full-pixel parameter space coordinate comparison unit 2130 is connected to the contrast line space-parameter space coordinate conversion unit 2120, and may accumulate the parameter space coordinate mapping curves by an accumulator in order to obtain a maximum parameter space coordinate of the parameter space coordinate mapping curves in a polar coordinate, so as to obtain a slant angle of the contrast line. The contrast line slant angle determining unit 2140 is connected to the full-pixel parameter space coordinate unit 2130, and may determine whether the slant angle is smaller than a default value predetermined by the contrast line slant angle determining unit 2140. When the slant angle is smaller than the default value, the refractive index of the analyte is obtained by a refractive index control unit 2150 according to a correspondence base of contrast line space coordinate and the refractive index, and transmit to the display module 220. When the slant angle is greater than the default value, the display module 220 may generate a reminding signal, so as to remind users whether the linkage between the optical device 10 and the electronic device 20 is deflected. That is, if the slant angle is greater than the default value, users are reminded to adjust the detachably optical device 10, and to recapture the image.

Embodiment

Figure 4:
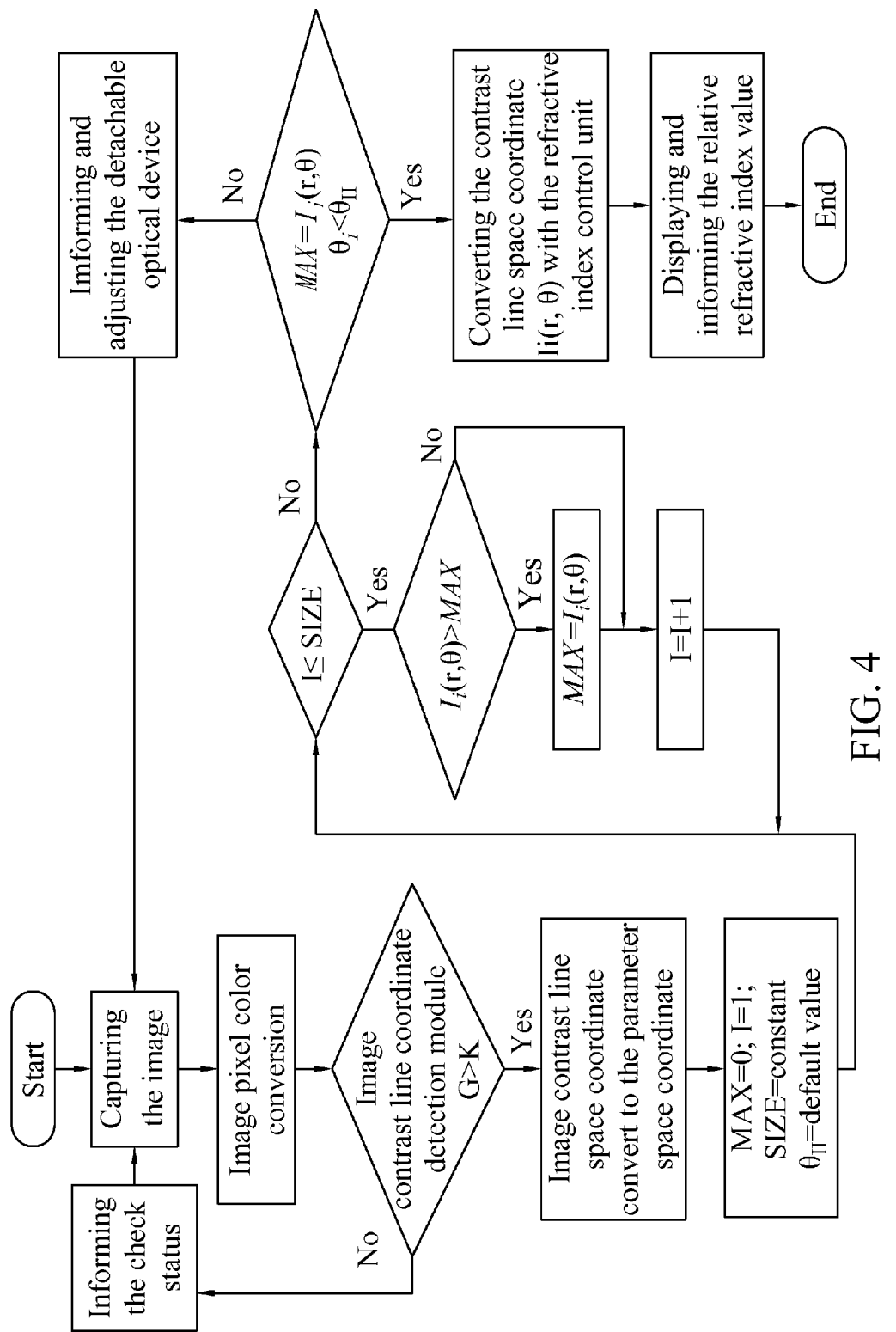
FIG. 4 is a flow diagram of the image-based refractive index measuring system according to the present invention.

With reference to FIG. 4, in which a flow diagram of the image-based refractive index measuring system according to the present invention is depicted. In the figure, first, the user switches on the image capture module 200 of the electronic device 20 to capture the light passing the analyte which is disposed in the optical device 10, and gather the external light via the analyte to generate the first image. The first image is a color two-dimensional image g(x,y) received by the image analyze module 210 which includes RGB three color components. A second image may be obtained after the image analyze module 210 executes the image pixel color conversion by a pixel conversion formula. The second image is a grayscale image h(x,y), the grayscale value is ranged from 0 to 255. After the image pixel color conversion is completed, the grayscale image is entered into the contrast line space coordinate detection unit 2110. The contrast line space coordinate detection unit 2110 conducts a convolution calculation with a horizontal Sobel operation mask (Mask_i) and a vertical Sobel operation mask (Mask_j), respectively, in order to obtain a horizontal gradient strength (Gi) and a vertical gradient strength (Gj) of each pixel point (x,y), the gradient value satisfies $G=\sqrt{(G_i)^2+(G_j)^2}$. The largest pixel point of the gradient strength G is the image edge and is also the pixel point of the contrast line.

It is worth noting, $$\text{Mask\_i} = \begin{bmatrix} 1 & 2 & 1 \\ 0 & 0 & 0 \\ -1 & -2 & -1 \end{bmatrix}, \text{Mask\_j} = \begin{bmatrix} -1 & 0 & 1 \\ -2 & 0 & 2 \\ -1 & 0 & 1 \end{bmatrix}.$$

Wherein, the horizontal gradient strength satisfies Gi=Mask_i*h(x,y), the vertical gradient strength satisfies Gj=Mask_j*h(x,y). If the threshold value K is a positive number and when the gradient value G of the image is smaller than the threshold value K, it is indicated that the device is abnormal. The user is informed that the check status is entered, the user checks whether the analyte is invalid or malfunction of other devices and re-capture images. When the gradient value G is larger than the threshold value K, the pixel points with the gradient value G larger than the threshold value K are regarded as contrast line characteristic points. An average value of the coordinate of all the contrast line characteristic points in the second image is calculated in order to obtain a contrast line of the second image and a contrast line space coordinate thereof to finish the determining of the contrast line and the mark of the position coordinate in the contrast line.

After the determination of the edge of the image contrast line and the mark of the contrast line position coordinate are completed, the process of conversion from the image contrast line space coordinate to the parameter space coordinate is performed. The contrast line space-parameter space coordinate conversion unit 2120 is arranged for converting all the contrast line characteristic points into a plurality of parameter space coordinate mapping curves according to a coordinate converting formula. The coordinate conversion formula is in compliance with the following equation: r=x cos θ+y sin θ; wherein, r is a distance between any pixel point (x,y) and the pole of the polar coordinate, θ is an angle between a polar axis and the line segment of the pixel point (x, y) and the pole of the polar coordinate.

If there is a tilt angle between the detachably optical device 10 and the electronic device 20, the contrast line of the analyte in the first image would also be skew. If the skew is more than the certain angle value, it represents that the optical device 10 and the electronic device 20 is overly tilt and the correctness of the measure of the refractive value may be affected. Therefore, the contrast line space-parameter space coordinate conversion unit 2120 may draw a parameter space coordinates mapping curve according to each characteristic point, and the full-pixel parameter space coordinate comparison unit 2130 is arranged for accumulating the parameter space coordinate mapping curves by an accumulator. That is, in the full-pixel parameter coordinate image, each pixel parameter coordinate Ii(r, θ) of each pixel all in the pixel space size may be checked and aligned one-by-one. If each pixel parameter coordinate Ii(r, θ) is not a maximum parameter space coordinate $I_{MAX}$ ($r_{MAX}$, $θ_{MAX}$), the process will be skipped to the next point (I=I+1, the initial value of I is 1) to continue checking. If the pixel parameter coordinate Ii(r, θ) is the maximum parameter space coordinate (MAX), the pixel parameter coordinate Ii(r, θ) of the maximum parameter space coordinate (MAX) is firstly stored, and the next point (I=I+1) would be checked until each pixel parameter coordinate Ii(r, θ) of all pixels in the pixel space size in order to obtain the maximum parameter space coordinate $I_{MAX}$($r_{MAX}$, $θ_{MAX}$) which is an intersection of the parameter space coordinates mapping curve. The $θ_{MAX}$ in the maximum parameter space coordinate $I_{MAX}$($r_{MAX}$, $θ_{MAX}$) is a maximum slant angle. Wherein, the initial value of the maximum parameter space coordinate $I_0$($r_0$, $θ_0$) is 0.

It is worth noting that the contrast line slant angle determining unit 2140 may determine whether the slant angle is smaller than a default value. If the slant angle is smaller than the default value, the refractive index of the analyte is obtained by the refractive index control unit 2150 according to a correspondence base of the contrast line space coordinate and the refractive index, and the refractive index is generated by the display module 220. On the contrary, the display module 220 will be generating a reminding signal to remind the user that the detachably optical device 10 should be adjusted and the image recaptured.

It is worth noting that the described above embodiment used the electronic device with a color image sensor, if the refractive index measuring system is implemented with the electronic device with a black-and-white image sensor, that would not exceed the scope of the present invention. The refractive index in the present invention may be utilized to detect the concentrations may be sugar content, sweetness or salinity.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:
1. An image-based refractive index measuring system, comprising:
   an optical device, arranged for guiding an external light passed through an analyte; and
   an electronic device, comprising;
   an image capture module, arranged for generating a first image by capturing the external light source;

an image analyze module connected to the image capture module, arranged for receiving the first image and analyzing the first image in order to generate an analytical result comprising a refractive index of the analyte; and a display module connected to the image analyze module, arranged for receiving and displaying the analytical result;

wherein, the optical device is detachably engaged to the electronic device, so as to guide the external light into the image capture module, wherein the image analyze module further comprises:
- a pixel conversion unit, arranged for converting the first image in order to obtain a second image via a pixel conversion formula;
- a contrast line space coordinate detection unit connected to the pixel conversion unit, arranged for analyzing the second image in order to obtain a gradient value G of each pixel point (x,y) in the second image, and determining at least one the pixel point (x,y) to be a contrast line characteristic point when the gradient value G of the pixel point (x,y) is greater than a threshold value K, and calculating an average value of each coordinate of all the contrast line characteristic points in the second image to obtain a contrast line of the second image and a contrast line space coordinate thereof;
- a contrast line space-parameter space coordinate conversion unit connected to the contrast line space coordinate detection unit, arranged for converting all the contrast line characteristic points into a plurality of parameter space coordinate mapping curves according to a coordinate converting formula;
- a full-pixel parameter space coordinate comparison unit connected to the contrast line space-parameter space coordinate conversion unit, arranged for accumulating the parameter space coordinate mapping curves by an accumulator in order to obtain a maximum parameter space coordinate of the parameter space coordinate mapping curves in a polar coordinate, so as to obtain a slant angle of the contrast line; and
- a contrast line slant angle determining unit connected to the full-pixel parameter space coordinate unit, arranged for determining whether the slant angle is smaller than a default value predetermined by the contrast line slant angle determining unit;

wherein, when the slant angle is smaller than the default value, the refractive index of the analyte is obtained by a refractive index control unit according to a correspondence table of contrast line space coordinate and the refractive index, and when the slant angle is greater than the default value, the display module generates a reminding signal.

2. The image-based refractive index measuring system of claim 1, wherein a color signal of the first image is converted to a grayscale signal by the pixel conversion formula in order to obtain the second image, the pixel conversion formula is in compliance with following equation:

$$gr=0.299*Ri+0.587*Gi+0.114*Bi;$$

wherein, Ri, Gi and Bi are color gradation values of red, green and blue respectively in the first image, gr is a grayscale value in the second image, the grayscale value is ranged from 0 to 255.

3. The image-based refractive index measuring system of claim 1, wherein a convolution calculation is conducted to each pixel point (x,y) in the second image with a horizontal Sobel operation mask (Mask_i) and a vertical Sobel operation mask (Mask_j), respectively, by the contrast line space coordinate detection unit in order to obtain a horizontal gradient strength (Gi) and a vertical gradient strength (Gj) of each pixel point (x,y), the gradient value satisfies $G=\sqrt{(G_i)^2+(G_j)^2}$.

4. The image-based refractive index measuring system of claim 1, wherein the coordinate conversion formula is in compliance with the following equation:

$$r=x \cos \theta + y \sin \theta;$$

wherein, r is a distance between any pixel point (x,y) and pole of the polar coordinate, θ is an angle between a polar axis and the line segment of the pixel point (x, y) and the pole of the polar coordinate.

5. The image-based refractive index measuring system of claim 1, the optical device comprising:
- a prism base having an accommodating space therein;
- a transparent window, arranged for obliquely laminating on one side of the prism base;
- a prism capable of producing a full reflection, disposed in the accommodating space of the prism base and laminated obliquely on the transparent window;
- an adapter lens having a side facing a terminal face of the prism; and
- a coupling element facing the adapter lens which nears an opposite side of the terminal face of the prism;

wherein, the optical device is detachably engaged to the electronic device through the coupling element.

6. The image-based refractive index measuring system of claim 5, wherein the coupling element is a magnetic component.

7. The image-based refractive index measuring system of claim 1, wherein the electronic device further comprises a sound reminding module that issues a high-frequency sound signal and a low-frequency sound signal respectively according to the comparison between a reference value and the refractive index.

8. The image-based refractive index measuring system of claim 7, wherein the sound reminding module issues the high-frequency sound signal when the refractive index is higher than a reference value or the sound reminding module issues the low-frequency sound signal when the refractive index is not higher than the reference value.

* * * * *